US008518327B2

(12) United States Patent
Kennedy et al.

(10) Patent No.: US 8,518,327 B2
(45) Date of Patent: Aug. 27, 2013

(54) INTEGRATED DISSOLUTION PROCESSING AND SAMPLE TRANSFER SYSTEM

(75) Inventors: Colin B. Kennedy, Greenbrae, CA (US); Syed Husain, Fremont, CA (US); Dale von Behren, Shrewsbury, MA (US); Rick Bernal, Westborough, MA (US)

(73) Assignee: Sotax Corporation, Horsham, PA (US)

( * ) Notice: Subject to any disclaimer, the term of this patent is extended or adjusted under 35 U.S.C. 154(b) by 0 days.

(21) Appl. No.: 13/437,414

(22) Filed: Apr. 2, 2012

(65) Prior Publication Data

US 2012/0255346 A1 Oct. 11, 2012

Related U.S. Application Data

(63) Continuation of application No. 11/648,050, filed on Dec. 28, 2006, now Pat. No. 8,158,059.

(60) Provisional application No. 60/755,025, filed on Dec. 30, 2005.

(51) Int. Cl.
*G01N 21/00* (2006.01)

(52) U.S. Cl.
USPC .................. 422/64; 422/50; 422/65; 422/66; 422/67; 422/500; 422/501; 422/502; 422/503

(58) Field of Classification Search
USPC ................................ 422/50, 64–67, 500–503
See application file for complete search history.

(56) References Cited

U.S. PATENT DOCUMENTS

| 4,879,917 A | 11/1989 | Eppelmann et al. |
| 5,816,701 A * | 10/1998 | Martin et al. ................. 366/208 |

FOREIGN PATENT DOCUMENTS

| EP | 0635713 | 1/1995 |
| WO | 02071033 | 9/2002 |

* cited by examiner

*Primary Examiner* — Jyoti Nagpaul
(74) *Attorney, Agent, or Firm* — Pepper Hamilton LLP

(57) ABSTRACT

The invention provides a system and method for dissolution testing. The system includes multiple dissolution vessels and a dose carrier positioned above the dissolution vessels. The dose carrier holds multiple removable carousels that receive individual doses for dissolution tested. Carousels that receive tablets or sinkers typically have a first configuration, while carousels that receive baskets typically have a second configuration. The two different configurations of carousels are interchangeable on the same dose ring. The system further includes a drive head positioned above the dose carrier, the drive head having a basket arbor and a mixing paddle removably and interchangeably attached. A pipettor integral with the system transfers sample aliquots having volumes in the range of 50 μl to 1 ml from the dissolution vessels to wells of an external receptacle.

9 Claims, 3 Drawing Sheets

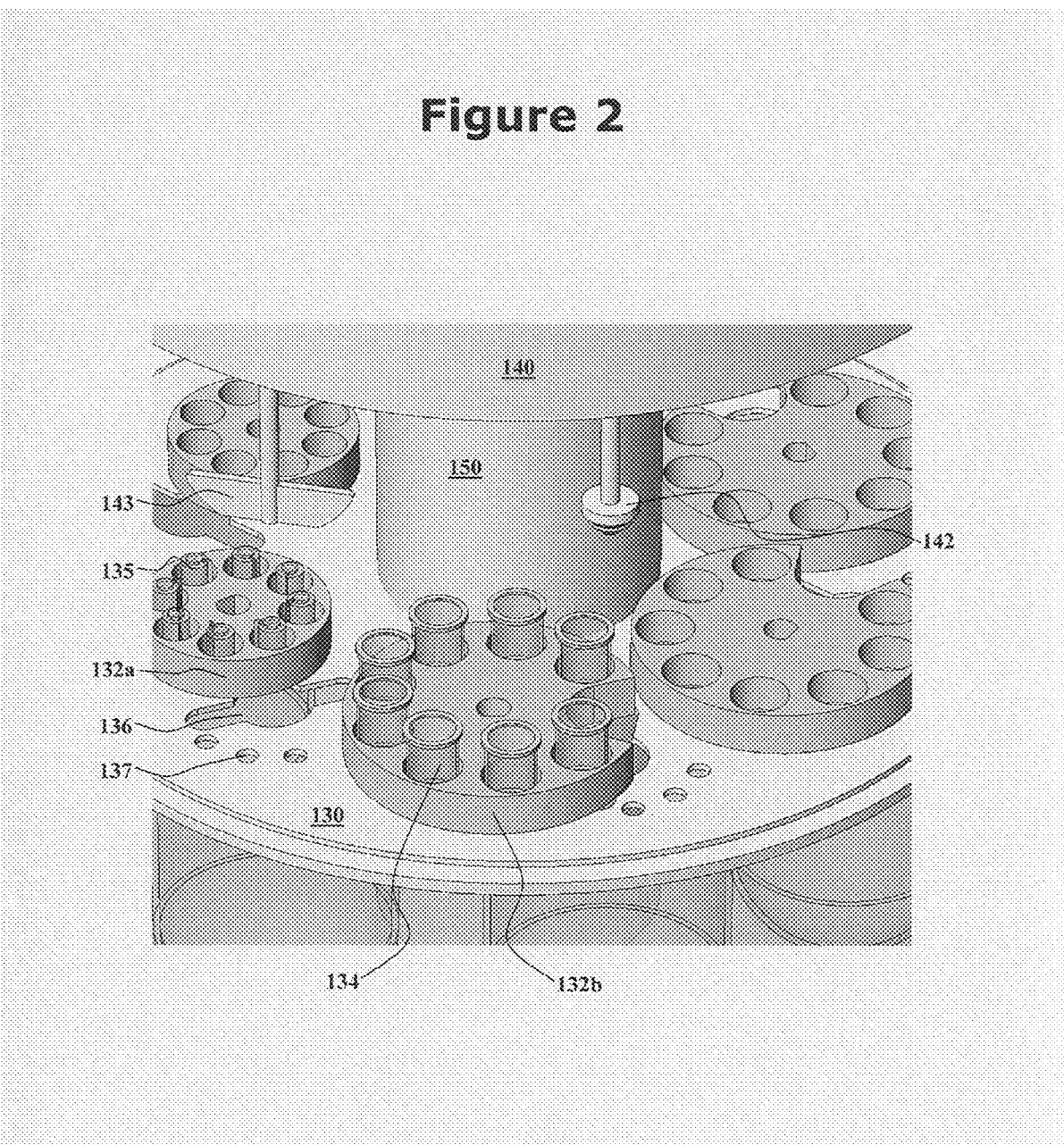

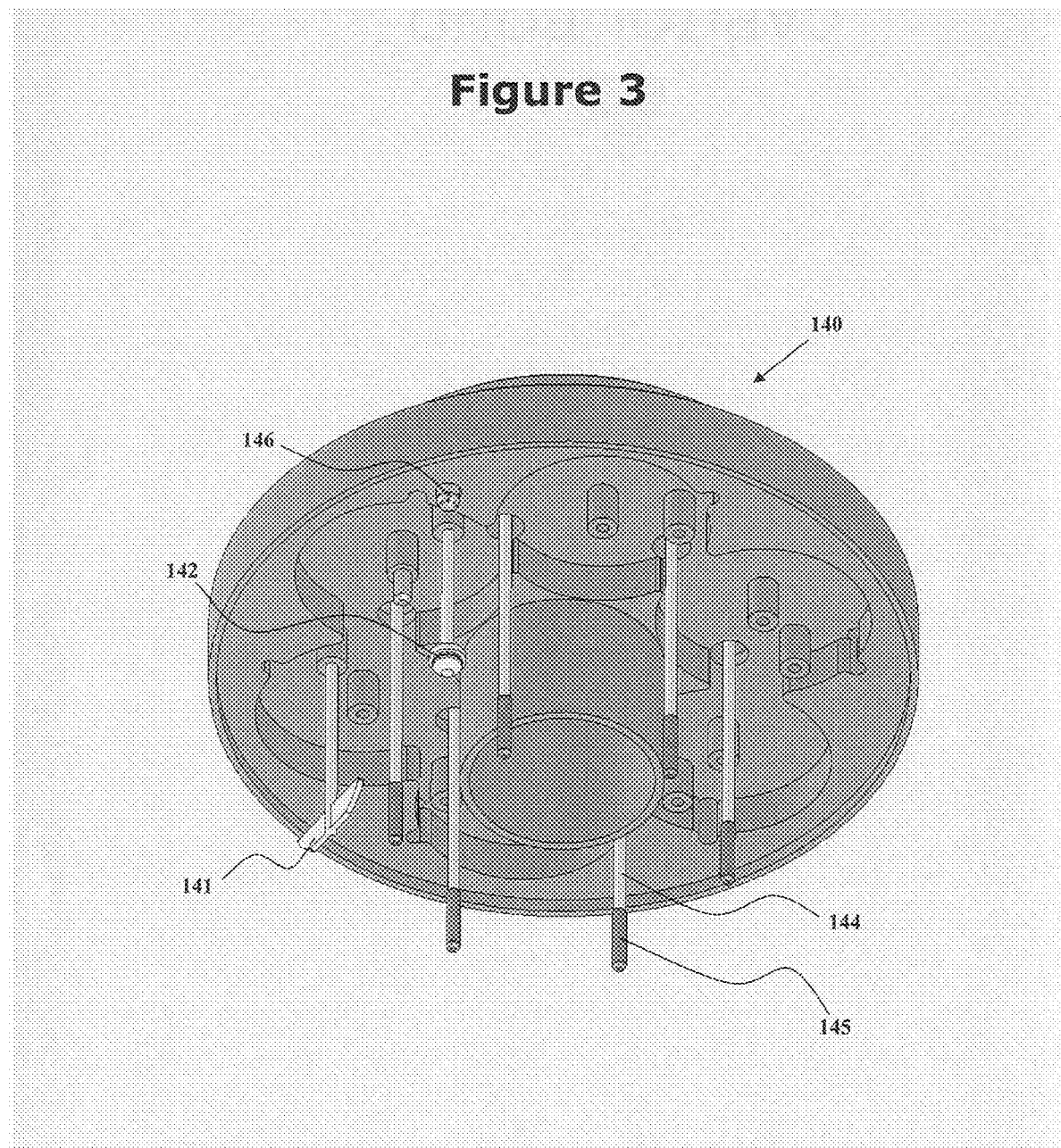

INTEGRATED DISSOLUTION PROCESSING AND SAMPLE TRANSFER SYSTEM

CROSS REFERENCE TO RELATED APPLICATION

This application claims the benefit of U.S. Provisional Application No. 60/755,025, filed Dec. 30, 2005, which is incorporated herein by reference in its entirety for all purposes.

TECHNICAL FIELD

This invention relates generally to the field of dissolution testing. More particularly, the invention relates to an integrated dissolution processing and sample transfer system.

BACKGROUND OF THE INVENTION

Dissolution testing involves physical evaluation of solid dosage forms such as capsules and tablets. Results of dissolution testing are useful in studying drug release characteristics of the dosage form and evaluating equipment and processes used in forming individual doses. To ensure uniformity in testing, entities such as the United States Pharmacopeia (USP) and the European Pharmacopeia provide guidelines for equipment used in dissolution testing.

Under these guidelines, typically a capsule or tablet is deposited in a test vessel containing dissolution media intended to emulate, for example, stomach or intestinal fluids. The vessel is maintained at a constant temperature, and the vessel contents are agitated at a specified speed. Samples of the resulting solution are then taken at predetermined times and analyzed using techniques such as high performance liquid chromatography (HPLC) and spectral analysis.

Conventional dissolution testing systems include pumps and tubing for transferring the samples from the test vessels to the analytical equipment. The samples transferred using such an arrangement may be as large as 10 ml. One disadvantage of using such large-volume samples is that the samples may contain undissolved particles that dissolve during the transfer process (termed secondary dissolution), resulting in inaccurate values for the dissolution rate. Another disadvantage of large-volume samples is that the vessel hydrodynamics are disrupted for the entire time the sample is being withdrawn from the vessel. For example, a typical transfer rate is 10 ml per minute, resulting in a full minute of disruption of the vessel hydrodynamics to withdraw a single 10-ml sample. In addition, withdrawing multiple large samples necessitates replenishing the sample media in the test vessel to maintain adequate volume for proper agitation of the mixture, adding complexity to the process.

Disadvantages of using tubing to transfer the samples include the inconvenience of purging the tubing after each sample is transferred and the risk of carryover (i.e., contamination) if purging is incomplete. Components of the sample may also adsorb to the inner surface of the tubing, producing an inaccurate dissolution rate.

Another disadvantage of prior art instruments is their inability to handle all possible dosage forms within a single test run or to handle the different dosage forms without modifying the instrument for each different dosage form. For example, some dosage forms, particularly capsules, float when placed into a fluid. These dosage forms must be inserted into "sinkers" that provide the needed additional weight to submerge the dosage form in the dissolution media. Alternatively, the dosage form may be inserted into a basket that is submerged in the dissolution media. Sinkers and tablets that sink can be placed directly into a dissolution vessel and agitated using a mixing paddle. The baskets themselves can be rotated or otherwise agitated, eliminating the need for a mixing paddle. Typically prior art systems are not able to handle tablets (and other dosage forms that are dispensed directly into the dissolution media) along with sinkers and baskets all within a single run. The dosage forms typically must be grouped by type and the instrument set up for that specific type of dosage form, often requiring modification of the system.

Therefore, it would be desirable to provide a dissolution testing system that overcomes the aforementioned and other disadvantages.

SUMMARY OF THE INVENTION

One aspect of the present invention is an integrated dissolution processing and sample transfer system. The system comprises a plurality of dissolution vessels. A dose carrier is positioned above the plurality of dissolution vessels. A first carousel is removably disposed on the dose carrier, the first carousel configured to receive a tablet. A second carousel is also removably disposed on the dose carrier, the second carousel configured to receive a basket, the basket configured to receive a capsule. A drive head is positioned above the dose carrier. A basket arbor and a mixing paddle are removably and interchangeably attached to the drive head.

Another aspect of the present invention is a method for dissolution testing. A dissolution testing system is provided, the system comprising a dose carrier, a first dissolution vessel, a second dissolution vessel, a first carousel, and a second carousel. A tablet is loaded into the first carousel. A capsule is loaded in a basket, and the basket is loaded into the second carousel. The first and second carousels are removably disposed on the dose carrier. Dissolution media is introduced into the first and second dissolution vessels. The tablet is submerged in the media in the first dissolution vessel, and the basket is submerged in the media in the second dissolution vessel.

Yet another aspect of the present invention is a computer-usable medium including a program for dissolution processing and sample transfer. The program comprises computer readable code for storing data representing the number of individual doses and types of dosage forms that have been loaded onto a dissolution processing and sample testing system; for introducing a volume of dissolution media into a dissolution vessel; for disposing an individual dose in the dissolution media within the dissolution vessel; for agitating the individual dose within the dissolution vessel; for removing an aliquot of sample solution from the dissolution vessel; and for delivering the sample solution aliquot to an external receptacle.

The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

BRIEF DESCRIPTION OF THE DRAWINGS

FIG. 2 is an enlarged view of a portion of the system of FIG. 1, showing carousels positioned on a dose ring; and FIG. 3 is an enlarged view of a portion of the system of FIG. 1, showing the underside of a drive head including cannulae, a basket arbor, and a mixing paddle.

DETAILED DESCRIPTION OF THE PRESENTLY PREFERRED EMBODIMENTS

Figure 1:
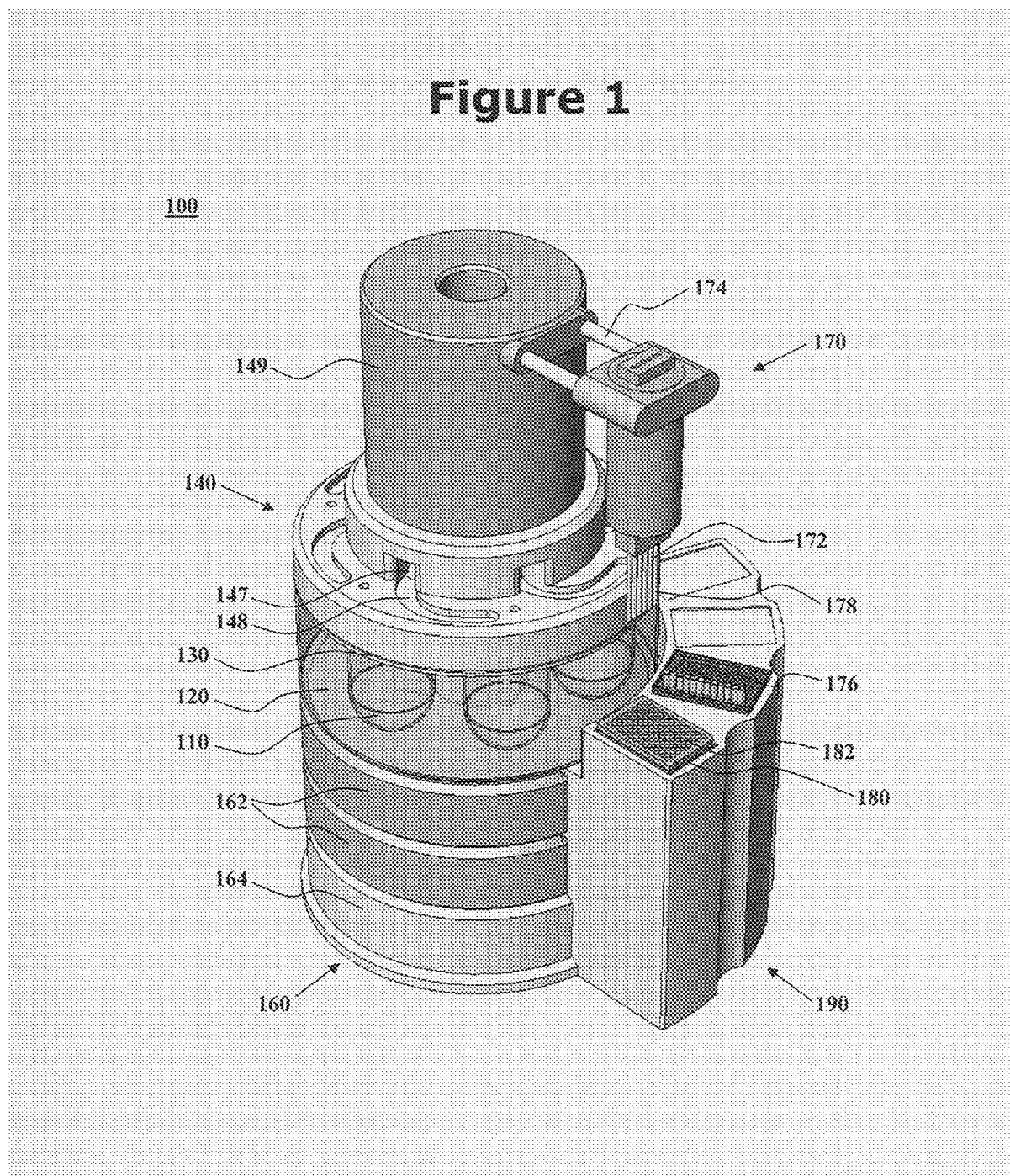
FIG. 1 is an isometric view of one embodiment of an integrated dissolution processing and sample transfer system.

One aspect of the present invention is an integrated dissolution processing and sample transfer system. One embodiment of the system, in accordance with the present invention, is illustrated at 100 in FIGS. 1-3. The illustrated system comprises a plurality of dissolution vessels 110, a water bath 120, a dose ring 130, a drive head 140, a central shaft 150, a base 160, a sample transfer device 170, an external receptacle 180, and an external receptacle support structure 190. Dose ring 130 includes removable carousels 132 configured with cavities 133 to receive baskets 134 or sinkers/tablets 135. Openings 136 and 137 are formed in dose ring 130. Drive head 140 includes fixtures 141 to hold a basket arbor 142 or a mixing paddle 143, cannulae 144 having electromagnets 145, a clean-in-place nozzle 146, sinker diversion structures 147, sinker collection trays 148, and a turret 149. Base 160 includes one or more tanks 162 as well as space 164 for components such as electronic controls (e.g., computer equipment) and plumbing. Sample transfer device 170, here a pipettor, includes pipettes 172 and a support arm 174. Pipettes 172 comprise disposable pipette tips 176 held by tip holders 178. External receptacle 180 includes wells 182.

In the embodiment illustrated in FIGS. 1-3, system 100 comprises a plurality of dissolution vessels 110 arranged in a circular array. While six vessels are included in the illustrated system, the number of vessels may be varied. Vessels 110 are immersed in water bath 120, which is heated to maintain the vessels at a desired temperature. Other methods for heating the vessels may be employed. For example the vessels may be positioned in cavities in a heated block, the cavities containing a small amount of fluid for transferring heat from the block to the vessels. In another alternative, an electrical resistance-type heater may be wrapped about each vessel.

A carrier for solid dosage forms, in the present embodiment dose ring 130, is positioned above the dissolution vessels. The dose ring can be raised and lowered on a central shaft 150 to provide access to the dissolution vessels. Dose ring 130 is configured to receive and actuate a plurality of removable carousels 132, one carousel for each dissolution vessel. The carousels are configured with cavities 133 to hold baskets 134 containing individual doses or, alternatively, to hold tablets or sinkers (sinkers/tablets 135). The term "tablet" is used herein to designate nonfloating dosage forms. Sinkers and baskets contain capsules, the term "capsule" being used herein to designate dosage forms that would otherwise float. Carousels holding tablets or sinkers typically have a first configuration (132a), while carousels holding baskets typically have a second configuration (132b). The two different configurations of carousels are interchangeable on the same dose ring. As illustrated in FIG. 2, each carousel 132 holds eight individual doses; however, the number of individual doses that are held by a carousel may be varied.

Dose ring 130 includes an opening 136 immediately adjacent to each carousel 132. In the embodiment illustrated in FIG. 2, each opening 136 comprises a circular aperture with two wing-like apertures extending outward from and connected to the circular aperture. This shape permits either a basket arbor 142 to which a basket is attached or, alternatively, an elongated mixing paddle 143 to pass through the opening and into the dissolution vessel below. The shape of opening 136 may be varied in other embodiments based, for example, on the shape of the basket and basket arbor and/or the shape of the mixing paddle. Openings 137 are provided in the dose ring to permit access to the dissolution vessel for purposes of, for example, introducing or withdrawing dissolution media from the dissolution vessels, washing the vessels, or for withdrawing aliquots of sample solutions. Additional openings (not shown) are positioned beneath the carousels to permit tablets or sinkers to be introduced into the dissolution vessels. The cavities in carousels 132a (i.e., those configured to hold tablets or sinkers) include movable bases that are automated to move aside at the appropriate time to allow a single tablet or sinker to fall through the carousel, through the opening positioned beneath the carousel, and into the dissolution vessel. Dose ring 130 includes a drive system (not shown) to rotate the carousels.

Drive head 140 is positioned above dose ring 130. The drive head rides up and down on a central shaft 150 and can be raised to facilitate loading of carousels onto the dose ring, to permit installation or removal of paddles and/or basket arbors, and to provide access to the dissolution vessels. The drive head is lowered during operation of the system.

Drive head 140 includes a plurality of fixtures 141 into which the basket arbors 142 or mixing paddles 143 may be installed. The basket arbors and paddles may be removable as well as interchangeable. Paddles 143 are configured to enter a dissolution vessel that holds a tablet or sinker. Basket arbors 142 are configured to pick up an individual basket from a carousel and deliver the removably attached basket into a dissolution vessel. Each basket arbor is fitted with an internal collet that expands or contracts to hold or release the basket. Other basket retention devices capable of holding and releasing a basket may be used. Baskets are automatically loaded onto and unloaded from the basket arbors by actions of drive head 140. For example, when drive head 140 is lowered, baskets 134 are automatically loaded onto arbors 142. When drive head 140 is raised, the baskets are automatically ejected from the arbors. Drives (not shown) may be provided in drive head 140 to rotate, oscillate, or otherwise move paddles and basket arbors within the vessels to facilitate dissolution of individual doses within the vessels.

Drive head 140 also includes one or more cannulae 144 that dispense media to dissolution vessels 110 before and during dissolution testing and aspirate dissolution mixtures from the vessels after testing has been completed. The term "cannula" as used herein refers to a tubular structure having a lumen for dispensing media. Cannulae 144 can be lowered to the bottoms of vessels 110 or raised above the liquid level of the vessel.

At least one clean-in-place nozzle 146 for washing vessels 110 using cleaning media (e.g., water or another appropriate fluid) is positioned on the drive head above vessels 110. In the embodiment illustrated in FIG. 1, tanks 162 for dissolution and cleaning media are located in base 160 of system 100, beneath water bath 120. Space 164 is provided in base 160 to accommodate components of the system such as electronic controls and plumbing (not shown). Alternatively, media tanks as well as system components may be located in units separate from the dissolution processing and sample transfer system and in fluid, electrical, or other appropriate communication with the system.

In one preferred embodiment, ends of cannulae 144 are equipped with electromagnets 145 that, when actuated, attract and capture sinkers 135 lying in the bottoms of the vessels. The cannulae are then raised to extract the sinkers from the vessels. Prior to the electromagnets releasing the sinkers, sinker diversion structures 147 move under the sinkers to prevent the sinkers from falling back into the vessels and direct the sinkers into, for example, sinker collection trays 148 arranged radially around the outside of drive head 140. A system operator can then retrieve the used sinkers from the collection tray.

Sample transfer device 170 extends from turret 149, which extends from drive head 140. In the present exemplary embodiment, sample transfer device 170 is a pipettor configured to collect a sample aliquot from each dissolution vessel 110 and dispense the sample aliquot into an external receptacle 180 such as a standard 96-well microplate, a microfluidic device having a well to receive the sample, or another sample receiving plate or vessel. Sample aliquot volumes are preferably in the range of 50 µl to 1 ml. External receptacle 180 is preferably a filter plate having multiple wells. As illustrated in FIG. 1, system 100 includes a support structure 190 configured to hold external receptacle 180 at a level that permits easy access to sample transfer device 170. Alternatively, a sample transfer device may be configured to access an external receptacle positioned separate from system 100.

In the embodiment illustrated in FIG. 1, sample transfer device 170 includes multiple pipettes 172 arranged in a linear array to permit samples to be collected individually from multiple dissolution vessels and delivered as a group to a multiwell external receptacle. In another embodiment, the pipettor device may include a single pipette or, alternatively, multiple pipettes arranged in a nonlinear array. Sample transfer device 170 has a support arm 174 that allows the device to move between dissolution vessels 110 and external receptacle 180. For example, support arm 174 may facilitate one or more of rotational motion, vertical motion, and horizontal motion of sample transfer device 170. Turret 149 of drive head 140 may also rotate about central shaft 150 to allow positioning of the sample transfer device for sample collecting and dispensing.

In one preferred embodiment, sample transfer device 170 is automated to pick up disposable pipette tips 176 prior to sampling and to eject the disposable pipette tips from tip holders 178 after the samples are delivered to the external receptacle, thereby preventing carryover or other sample contamination. After disposable pipette tips 176 are ejected, each tip holder 178 is capable of mating with a filter plate well 182, forming a pressure seal around the well. Pressure may then be exerted on the well via the tip holder, forcing the sample through the filter and into the sample well beyond the filter, ensuring only dissolved material is present in the sample well. The sample transfer device may also be capable of subsequent sample manipulation, for example permitting dilution of the sample if this is desired. The system includes programming for automating the above-mentioned and other tasks.

An integrated dissolution processing and sample transfer system may be varied in numerous ways. In one variation, in the embodiment described above, access to the dissolution vessels and dose ring may be provided by portions of the system being removable or being movable by means other than riding up and down on a central shaft. For example, multiple shafts may be employed to raise and lower portions of the system to provide access to the dissolution vessels and dose ring.

In another variation, rather than the dissolution vessels being arranged in a circular array, the vessels may form one or more linear arrays with the sample transfer device configured to sample from the vessels and dispense to the external receptacle(s) along a linear path. Alternatively, the dissolution vessels may be laid out in any configuration that permits an integrated sample transfer device to sample from the vessels and dispense directly to the external receptacle(s). In yet another variation, a portion of the system need not be raised to permit access to the dissolution vessels, which are hinged and rotatable to open for loading, cleaning, and other setup or maintenance tasks.

Another aspect of the present invention is a method for dissolution testing. The method is carried out using a dissolution testing system. For example, the method may be carried out using a dissolution processing and sample transfer (DPST) system such as has been described above and illustrated in FIGS. 1-3 at 100.

Individual doses are loaded into carousels. The carousels may be removed from the DPST system and taken to a work bench for loading. The doses may be placed directly into cavities in the carousel, or they may be inserted into sinkers or baskets prior to being placed into the carousel cavities. Sinkers and tablets are placed in carousels having a first configuration (e.g., 132a), while baskets are placed in carousels having a second configuration (e.g., 132b). Once the carousels have been filled, they are loaded onto the DPST system, onto a dose ring such as is best seen at 130 in FIG. 2. Using system 100, carousels holding sinkers and tablets may be intermixed with carousels holding baskets on the same dose ring 130.

Basket arbors 152 and/or mixing paddles 153 are inserted into fixtures 151, with basket arbors positioned above carousels holding baskets, and mixing paddles positioned above carousels holding sinkers and/or tablets. Alternatively, basket arbors and/or mixing paddles may already be installed, removably or permanently, in the DPST system.

The system is initiated, for example by programming the system for the number of individual doses and type of dosage forms that have been loaded onto the system. In response to being initiated, the system automatically carries out the programmed steps for dissolution processing and sample transfer. Such steps may include all or some of the following actions.

Dissolution media is introduced into all or some of the vessels, and the media within the vessels is heated to a previously specified temperature. An individual dose is submerged in the media within each vessel. This may be accomplished by picking up a basket with a basket arbor and inserting the removably attached basket into the dissolution vessel or, alternatively, by dropping a tablet/sinker into the dissolution vessel through the base of the cavity holding the tablet/sinker and inserting a mixing paddle into the vessel. The individual doses are then agitated by movement of the basket arbor and attached basket or by movement of the mixing paddle.

Once the individual doses have been agitated within the vessels for the predetermined length of time, an aliquot of sample solution is withdrawn from each vessel. This is preferably accomplished using an integrated sample transfer device such as the pipettor shown at 170 in FIG. 1. The automated pipettor picks up disposable pipette tips 176, accesses each dissolution vessel through an opening provided for this purpose, withdraws a sample solution aliquot from each dissolution vessel, and delivers the sample solution aliquots to an external receptacle such as is shown at 180 in FIG. 1.

The automated pipettor then moves away from the external receptacle and ejects disposable pipette tips 176 from tip holders 178. Where external receptacle 180 is, for example, a multiwell plate having a plurality of open reservoirs, the plate may then be removed from the dissolution processing and sample transfer system and transferred to, for example, a high performance liquid chromatography (HPLC) or spectral analysis instrument.

In one preferred embodiment, external receptacle 180 is a filter plate. In this embodiment, pipettor 170 returns to the external receptacle after ejecting the disposable pipette tips, and each tip holder 178 mates with a filter plate well 182, forming a pressure seal around the well. Pressure is then be exerted on the well via the tip holder, forcing the sample through the filter and into the sample well beyond the filter. Once all of the filter plate wells have been similarly treated using the tip holders, the filter plate may be removed from the DPST system and transferred to a testing instrument.

In one preferred embodiment, the DPST system may be programmed to carry out serial sampling over time of each dissolution vessel, placing the serial samples in a single or multiple external receptacles. If desired, additional sample processing steps may be carried out prior to removing an external receptacle from the DPST system. For example, the samples may be diluted or otherwise treated in preparation for testing.

Yet another aspect of the present invention is a computer-usable medium including a program for dissolution processing and sample transfer comprising computer readable code for the following: storing data representing the number of individual doses and type(s) of dosage forms that have been loaded onto the system; introducing the correct volume of dissolution media into some or all of the dissolution vessels; disposing an individual dose in the dissolution media within each dissolution vessel; agitating the individual dose within each dissolution vessel; withdrawing an aliquot of sample solution from each dissolution vessel; delivering each sample solution aliquot to an external receptacle; and performing additional processing steps, including, but not limited to, sample dilution.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for dissolution testing, comprising:
 a plurality of dissolution vessels;
 a dose carrier positioned above the plurality of dissolution vessels;
 a first carousel removably disposed on the dose carrier, wherein the first carousel is configured to receive a dosage form;
 a drive head positioned above the dose carrier;
 a heating element to maintain the dissolution vessels at a desired temperature; and
 a sample transfer device integral with the system.

2. The system of claim 1 wherein the first carousel is configured to receive a basket, wherein the basket is configured to receive a dosage form.

3. The system of claim 1 further comprising a second carousel removably disposed on the dose carrier, wherein either the first carousel or the second carousel is configured to receive a basket, wherein the basket is configured to receive a dosage form.

4. The system of claim 1 wherein the dissolution vessels are arranged in a circular array.

5. The system of claim 1 wherein the heating element is a water bath, a heating block, or an electrical resistance-type heater.

6. The system of claim 1 further comprising an external receptacle support structure configured to receive an external receptacle.

7. The system of claim 6 further comprising an external receptacle positioned to receive a sample from the sample transfer device.

8. The system of claim 7 wherein the external receptacle is a microfluidic device having a well.

9. The system of claim 8 wherein the microfluidic device is a 96-well microplate or a filter plate having multiple wells.

* * * * *